United States Patent
Kolari et al.

(10) Patent No.: US 9,341,560 B2
(45) Date of Patent: May 17, 2016

(54) DEVICE AND METHOD FOR MONITORING BIOCIDE DOSING IN A MACHINE

(71) Applicant: KEMIRA OYJ, Helsinki (FI)

(72) Inventors: Marko Kolari, Vantaa (FI); Tuija Suhonen, Siuntio KK (FI); Jukka-Pekka Sirvio, Espoo (FI); Iiris Joensuu, Espoo (FI)

(73) Assignee: KEMIRA OYJ (FI)

( * ) Notice: Subject to any disclaimer, the term of this patent is extended or adjusted under 35 U.S.C. 154(b) by 0 days.

(21) Appl. No.: 14/373,236

(22) PCT Filed: Jan. 21, 2013

(86) PCT No.: PCT/FI2013/050060
§ 371 (c)(1),
(2) Date: Jul. 18, 2014

(87) PCT Pub. No.: WO2013/107941
PCT Pub. Date: Jul. 25, 2013

(65) Prior Publication Data
US 2015/0000853 A1     Jan. 1, 2015

Related U.S. Application Data

(60) Provisional application No. 61/588,710, filed on Jan. 20, 2012.

(51) Int. Cl.
*G01N 17/04* (2006.01)
*D21H 21/36* (2006.01)
(Continued)

(52) U.S. Cl.
CPC .............. *G01N 17/04* (2013.01); *D21H 21/04* (2013.01); *D21H 21/36* (2013.01); *D21H 23/20* (2013.01); *G01N 27/041* (2013.01)

(58) Field of Classification Search
CPC ....... D21H 21/36; D21H 21/04; D21H 21/38; D21H 23/20; D21H 23/78; G01N 17/04; G01N 27/04; G01N 33/343; G01N 27/041; A01N 59/00; C02F 2103/28; C02F 1/76; C02F 2303/08; C23F 11/00; C23F 14/02; C23F 15/00
USPC .......................... 162/198, 199, 160–161, 252; 700/127–129
See application file for complete search history.

(56) References Cited

U.S. PATENT DOCUMENTS

| 2,898,026 A | * | 8/1959 | Aid ............................... 206/205 |
| 5,894,040 A | * | 4/1999 | Foley et al. ................. 428/34.2 |

(Continued)

FOREIGN PATENT DOCUMENTS

| CN | 1359430 A | 7/2002 |
| CN | 2577275 Y | 10/2003 |

(Continued)

OTHER PUBLICATIONS

Search Report, State Intellectual Property Office of the People's Republic of China; 2 pages, regarding application No. 201380006117.4; dated Jun. 15, 2015.

(Continued)

*Primary Examiner* — Jose Fortuna
(74) *Attorney, Agent, or Firm* — Thomas Horstemeyer, LLP

(57) ABSTRACT

Embodiments of the present disclosure include methods to control the quantity of vapor phase corrosion, devices, and the like.

10 Claims, 3 Drawing Sheets

(51) Int. Cl.
  *D21H 21/04*  (2006.01)
  *D21H 23/20*  (2006.01)
  *G01N 27/04*  (2006.01)

(56) References Cited

U.S. PATENT DOCUMENTS

| | | | |
|---|---|---|---|
| 7,759,265 B2* | 7/2010 | Elkouh et al. | 442/86 |
| 7,776,363 B2* | 8/2010 | Rice et al. | 424/661 |
| 7,829,305 B2* | 11/2010 | Kolari et al. | 435/32 |
| 8,085,165 B2* | 12/2011 | Wavering et al. | 340/870.02 |
| 8,133,383 B2* | 3/2012 | Hammonds et al. | 205/775.5 |
| 8,273,382 B2* | 9/2012 | Rice et al. | 424/661 |
| 8,282,778 B2* | 10/2012 | Kolari | 162/161 |
| 8,323,417 B2* | 12/2012 | Fan et al. | 134/6 |
| 8,419,899 B2* | 4/2013 | Xia et al. | 162/161 |
| 8,506,777 B2* | 8/2013 | Hammonds et al. | 204/404 |
| 8,578,781 B2* | 11/2013 | Dahlstrom | 73/700 |
| 8,709,206 B2* | 4/2014 | Xia et al. | 162/161 |
| 8,795,589 B1* | 8/2014 | Furman et al. | 422/9 |
| 8,858,717 B2* | 10/2014 | Fan et al. | 134/10 |
| 8,906,202 B2* | 12/2014 | Grattan et al. | 162/198 |
| 8,933,244 B2* | 1/2015 | Janak et al. | 548/322.5 |
| 8,986,606 B2* | 3/2015 | Nelson et al. | 422/7 |
| 9,018,141 B2* | 4/2015 | Kolari et al. | 507/130 |
| 2006/0120916 A1* | 6/2006 | Kolari et al. | 422/28 |
| 2006/0198954 A1* | 9/2006 | Frechem et al. | 427/212 |
| 2007/0098932 A1* | 5/2007 | Rudolph et al. | 428/34.2 |
| 2008/0204275 A1* | 8/2008 | Wavering et al. | 340/870.16 |
| 2009/0012825 A1* | 1/2009 | Ng | 705/7 |
| 2010/0267791 A1* | 10/2010 | Kolari et al. | 514/389 |
| 2011/0200688 A1* | 8/2011 | Harvey et al. | 424/723 |
| 2013/0101682 A1* | 4/2013 | Rice et al. | 424/665 |
| 2013/0101683 A1* | 4/2013 | Tu et al. | 424/665 |
| 2013/0153510 A1* | 6/2013 | Jansson et al. | 210/727 |
| 2013/0164814 A1* | 6/2013 | Sarja et al. | 435/184 |
| 2013/0191038 A1* | 7/2013 | Wolf | G01N 17/04 702/34 |
| 2013/0220922 A1* | 8/2013 | Joensuu et al. | 210/632 |
| 2014/0116138 A1* | 5/2014 | Sheverev | G01N 17/008 73/579 |
| 2014/0151273 A1* | 6/2014 | Lehikoinen et al. | 209/164 |
| 2014/0242191 A1* | 8/2014 | Kolari et al. | 424/641 |
| 2014/0367334 A1* | 12/2014 | Salonen et al. | 210/636 |
| 2015/0000853 A1* | 1/2015 | Kolari et al. | 162/252 |
| 2015/0268153 A1* | 9/2015 | Johannes | G01N 17/04 205/775.5 |

FOREIGN PATENT DOCUMENTS

| | | | | |
|---|---|---|---|---|
| CN | 101363791 A | | 2/2009 | |
| CN | I02004074 A | | 4/2011 | |
| CN | I02749280 A | | 10/2012 | |
| WO | WO 0066810 A1 | * | 11/2000 | C23F 11/08 |
| WO | WO 2004040983 A1 | * | 5/2004 | A01N 65/00 |
| WO | WO 2004042082 A1 | * | 5/2004 | C12Q 1/68 |
| WO | WO 2005045132 A1 | * | 5/2005 | D21H 21/04 |
| WO | 2007089539 A2 | | 8/2007 | |
| WO | WO 2007089539 A3 | * | 11/2007 | |
| WO | WO 2008056025 A2 | * | 5/2008 | C02F 1/50 |
| WO | 2008115050 A1 | | 9/2008 | |
| WO | WO 2008115050 A1 | * | 9/2008 | G01N 17/00 |
| WO | WO 2009143511 A1 | * | 11/2009 | D21F 1/66 |
| WO | 2011037819 A1 | | 3/2011 | |

OTHER PUBLICATIONS

Li Jivaing et al. "Chapter 13 Industrial Corrosion monitoring technology"; May 2007, pp. 229-232; (place unknown).

* cited by examiner

Modified ER probe

Cross-sectional view

DEVICE AND METHOD FOR MONITORING BIOCIDE DOSING IN A MACHINE

CROSS-REFERENCE TO RELATED APPLICATIONS

This application is the 35 U.S.C. §371 national stage of PCT Application No. PCT/FI2013/050060, filed Jan. 21, 2013, which is herein incorporated by reference in its entirety and which also claims priority to, and the benefit of, U.S. Provisional Application No. 61/588,710, filed Jan. 20, 2012, which is herein incorporated by reference in its entirety.

FIELD

The present invention relates to an improved method for minimizing corrosion damages of machinery for paper or board manufacturing.

BACKGROUND

Microorganisms are present in paper and board machines every day. Their entry into the process is inevitable, because the circulating water contains biodegradable dissolved substances, temperature and pH are typically favourable for microbial life, and the machines are open processes subject to contaminants from air, water, and non-sterile raw materials. Paper and board machines can support growth of very different kinds of microorganism; but most common organisms are bacteria and fungi. A thorough review of paper machine microbiology, about the microorganisms and their impact on paper making, is presented in Chapter 6: Paper machine microbiology, pp. 181-198, by Marko Kolari, in Handbook of Papermaking chemistry 2007, Raimo Alen (Ed.), Finnish Paper Engineers' Association, Helsinki, Finland.

Microorganisms can cause a number of problems in papermaking, if countermeasures are not taken. Microbes may affect both the functioning of the chemistry of papermaking and the quality of the end product. Starch is one of the most easily digestible nutrients for microbes, but also some other additive slurries are prone to spoilage. High microbial activity, for example in a coated broke tower, can lower the pH and thus have a marked effect on wet-end chemistry. High microbial activity can also create strong odours that may be a nuisance or even a danger to personnel, and also destructive for product quality in packaging grades. Slime formation (biofilms) on the surfaces of tanks and machine frames leads to paper defects (spots and holes) or web breaks when slime lumps are sloughing off. A web break requires cleaning and re-starting, results in system down-time, lost paper production, reduced efficiency and increased costs. It is therefore desirable to both minimize bacteria in the process waters and to prevent biofilm formation on the system surfaces.

Biocide dosing to the process waters is the most common way to combat microbes. A typical biocide program is composed of individual treatments of the different parts of the process system, such as incoming raw water, additive storages, paper machine water circuits, and the broke system. If biocide treatment in one part fails, it typically affects the whole machine. The type of biocide to be selected depends on the point of application, the performance target and chemical compatibility to the system. In the treatment of paper machine wet-end, i.e. circulating water and broke system, oxidizing biocides are nowadays widely used due to their cost-efficiency. Common oxidizing biocides are for example the "free halogen" sources such as sodium hypochlorite, hypobromous acid and chlorine dioxide. Also widely used are so called "stabilized halogens" such as halogenated hydantoins, e.g., bromochloro-dimethylhydantoin or partially halogenated hydantoins such as monochloro-dimethylhydantoin. Other common "stabilized halogen" oxidizing biocides are haloamines, such as chloramines and bromamines, formed by combining an ammonium source, such as ammonium sulfate, ammonium chloride, ammonium bromide, ammonium phosphate, ammonium nitrate or any other ammonium salt, including urea, with an oxidant such as sodium hypochlorite.

The possibility to prevent microbial problems in a cost-effective manner has been the driving force making the oxidizing biocides as the preferred biocide type in most of the paper machines. However, now the longer-term use of some of the oxidizing biocides has created a new type of problem, namely vapor phase corrosion of machinery. The different oxidizing biocide chemistries do differ in terms of volatility and life-time in the paper machine process water. In case of using extensive dosages of an oxidizing biocide type that cycles-up in the process water, and is also very volatile, this can lead to vapor phase corrosion problems. Most volatile oxidizing biocides are chlorine dioxide and haloamines. In worse cases, the corrosion of paper machinery in the beginning of drying section has created huge runnability problems and deteriorated the paper quality due to flakes of corrosion products detaching from the damaged parts of the machinery.

Corrosion is a particular concern in the "short loop," or short circulation section, of a paper machine, and in the subsequent press and drying section. In a typical pulp and paper process, pulp stock is passed into a headbox, which distributes the pulp stock onto a moving wire in a forming section. The paper sheet is formed in the forming section and then sent to presses and dryers for finishing. The short loop is a system that re-circulates and recycles excess water from the pulp stock. The excess water is collected in a wire pit in the forming section and then a major portion thereof is recirculated back to the headbox for re-use. Although many tanks, lines and other immersed structures of pulp and paper systems are typically formed from acid-proof stainless steel, many components above the water surface level, and in the press and dryer section, are formed from milder steel materials. So these components can be adversely affected by vapor phase corrosion taking place due to intense use of volatile type of oxidizing biocides for microbe control.

The current practice of how paper makers are following vapor phase corrosion (if monitoring at all) is based on installing steel coupons (e.g., carbon steel coupons) hanging in the vicinity of the paper machine. These coupons have been accurately weighted before installation and after removal they are thoroughly washed to remove any loose corrosion products, dried and weighted again. The corrosion rate is calculated based on metal loss (weight loss) during the exposure time. Monitoring with corrosion coupons only provides delayed information and does not allow a fast reaction time. Thus, there is a need to try to overcome at least these problems.

SUMMARY OF THE INVENTION

In accordance with the purpose(s) of the present disclosure, as embodied and broadly described herein, embodiments of the present disclosure, in one aspect, relate to methods to monitor and/or control the quantity of vapor phase corrosion, devices, and the like.

In one aspect, the present invention provides, a method for monitoring the vapor phase corrosion in a paper or board machine comprising obtaining information regarding the rate of vapor phase corrosion over a time period; and using the information to determine how to adjust the dosing of an oxidizing biocide in a paper or board making process.

In another aspect a modified ER device comprising an ER probe and a cooling unit is provided.

In yet another aspect, a method comprising obtaining, by a computing device, information regarding the rate of vapor phase corrosion over a time period; and using the information to determine, by a computing device, how to adjust the dosing of an oxidizing biocide in a paper or board making process, is provided.

In yet another aspect, a system comprising at least one computing device; and a method application executable in the at least one computing device, the method application comprising: logic that obtains information regarding the rate of vapor phase corrosion over a time period; and logic that uses the information to determine how to adjust the dosing of an oxidizing biocide in a paper or board making process, is provided.

Other structures, methods, features, and advantages will be, or become, apparent to one with skill in the art upon examination of the following drawings and detailed description. It is intended that all such additional structures, systems, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
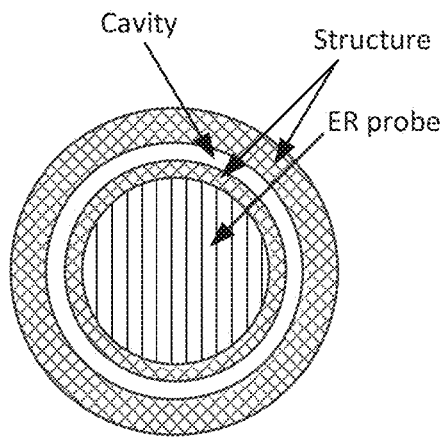
FIG. 1 illustrates a cross-sectional view of an embodiment of the present disclosure.

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Embodiments of the present disclosure will employ, unless otherwise indicated, techniques of paper science, chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, dimensions, frequency ranges, applications, or the like, as such can vary. It is also to be understood that the terminology used herein is for purposes of describing particular embodiments only, and is not intended to be limiting. It is also possible in the present disclosure that steps can be executed in different sequence, where this is logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

In the first aspect, the present invention provides a method for monitoring the vapor phase corrosion in a paper or board machine. It comprises the steps of obtaining information regarding the rate of vapor phase corrosion over a time period; and using the information to determine how to adjust the dosing of an oxidizing biocide in a paper or board making process. Preferably, the information is obtained using a modified electrical resistance (ER) probe equipped with an ER probe and a cooling unit disposed around the ER probe. The information includes preferably measurement information of the corrosion or determination of the corrosion rate by measurements. Preferably, the information is obtained using a temperature measurement sensor to measure the temperature of one or more of the following: the ER probe, the air around the ER probe, or the air outside of the ER probe. Preferably, the amount of the oxidizing biocide is adjusted based on the information obtained regarding vapor phase corrosion. Preferably, the amount of the oxidizing biocide is adjusted based on the information obtained regarding vapor phase corrosion. Obtaining information preferably includes measuring an electrical resistance of an element in the modified ER probe. Preferably, an increase in the electrical resistance of the element over a time period indicates that the element undergoes reduction, and a rate of corrosion is determined from the reduction of the element over the time period. The method preferably further comprises controlling the temperature difference between the air outside of the modified ER probe and the surface of the ER probe.

The method may be modified by assisting the data collection and the use of information by a computing device. In another aspect, a method is provided comprising obtaining, by a computing device information regarding the rate of vapor phase corrosion over a time period; and using the information to determine, by a computing device, how to adjust the dosing of an oxidizing biocide in a paper or board making process. The method preferably further comprises adjusting, by the computing device, the amount of the oxidizing biocide based on the information obtained regarding vapor phase corrosion. The information obtained preferably includes measuring, by the computing device, an electrical resistance of an element in a modified ER probe. The method preferably further comprises controlling, by a computing device, the temperature difference between the air outside of a modified ER probe and a surface of an ER probe.

In yet another aspect, the present invention provides a modified electrical resistance (ER) device. It comprises an ER probe and a cooling unit. This device is suitable for use in the above described methods for monitoring the vapor phase corrosion in a paper or board machine described in the first aspect. The cooling device of the modified ER probe preferably includes a structure disposed around the ER probe, wherein a cavity is formed between the structure and the ER probe, and wherein the structure includes one or more openings. Preferably, the cooling device is configured to flow a cooling medium in the cavity. In one embodiment, the cooling device is directly attached to the ER probe to control the temperature of the ER probe. In another embodiment, the cooling device is not directly attached to the ER probe, and the cooling medium is used to control the temperature of the ER probe. Preferably, the modified ER probe further comprises a temperature measurement sensor to measure the temperature of one or more of the following: the ER probe, the air around the ER probe, or the air outside of the ER probe.

A yet further aspect of the present invention is a system able to perform the required processes described above. This system comprises at least one computing device; and a method application executable in the at least one computing device, the measuring application comprising: logic that obtains information regarding the rate of vapor phase corrosion over a time period; and logic that uses the information to determine how to adjust the dosing of an oxidizing biocide in a paper or board making process. The system preferably further comprises logic that adjusts the amount of the oxidizing biocide based on the information obtained regarding vapor phase corrosion. Obtaining information preferably includes logic that measures an electrical resistance of an element in a modified ER probe. The system preferably further comprises logic that controls the temperature difference between the air outside of a modified ER probe and a surface of an ER probe.

By method application is meant the means for carrying out a method for monitoring the vapor phase corrosion in a paper or board machine, comprising obtaining information regarding the rate of vapor phase corrosion over a time period; and using the information to determine how to adjust the dosing of an oxidizing biocide in a paper or board making process, as described above or means for measuring or determining the required elements in a measuring application. The method application is typically implemented by portions of computer software executable in a computing device.

By logic is meant portions of computer software which are executed in a computing device causing the computing device to perform logical operations as defined in the method for monitoring the vapor phase corrosion in a paper or board machine, comprising obtaining information regarding the rate of vapor phase corrosion over a time period; and using the information to determine how to adjust the dosing of an oxidizing biocide in a paper or board making process, as described above or means for measuring or determining the required elements in a measuring application.

The various aspects of the present invention are further described by the following embodiments.

Embodiments of the present disclosure include methods to monitor and/or control the quantity of vapor phase corrosion, devices, and the like. In particular, embodiments of the present disclosure can include monitoring the rate and/or quantity of vapor phase corrosion of paper machinery (e.g., uniform corrosion) on-line. In an embodiment, the rate and/or quantity of vapor phase corrosion can be used to control the dosing amounts of oxidizing biocides as an effective way to minimize vapor phase corrosion in a paper machine in a timely manner.

One or more embodiments of the present disclosure relate to an improved method for minimizing corrosion damages of machinery for paper or board manufacturing, and in particular, minimizing corrosion damages caused by dosing of biocides to said aqueous manufacturing process. This can be accomplished by use of modified ER probe as an on-line vapor-phase corrosion sensor for monitoring corrosion rate and by use of that information for adjusting biocide dosing in time.

An exemplary embodiment of the present disclosure can be advantageous over the current methods where information on corrosion rate is based on weight loss information from corrosion coupons that have been held in the process for several weeks. Other methods provide information with a significant time delay only and there is not an opportunity to react quickly in changes in corrosiveness.

An exemplary embodiment of the present disclosure enables the use of on-line and real-time or semi-real-time information on the corrosion rate that can be directly used for adjusting oxidizing biocide dosing quantity and thus, e.g., sudden peaks with high corrosion rate can be stopped in a timely fashion (e.g., hours or days). In general, the oxidizing biocide can be added to one or more points in the process and these can include the pulp line, water line, or tanks.

An exemplary embodiment of the present disclosure includes monitoring the rate of vapor phase corrosion of paper machinery on-line and using that information to control the dosing amounts of oxidizing biocides. Monitoring the corrosion in this manner can be an effective way to minimize vapor phase corrosion in a paper machine.

In addition, an exemplary embodiment of the present disclosure includes an on-line sensor based on a modified Electrical Resistance (ER) probe, such as electrical resistance technique, that can be used as an on-line sensor, which can be used to determine if the amount of biocide should be adjusted (e.g., manually or automatically adjusting biocide dosing pumps). In an embodiment, the modified ER probe can be part of a modified ER probe system. In an exemplary embodiment, the ER probe can be equipped with an ER probe and a cooling unit and optionally a temperature measurement device. In an embodiment, the cooling unit enables the formation of condensate water on the probe surface. In an embodiment, the modified ER probe, such as a cooling unit and temperature measurement device, can be in communication with a computer system, such as including an on-line data collection system, a data interpretation system, a control system for the cooling unit, and the like. In an embodiment, the modified ER probe may include one of the ER probes sold by CAPROCO or ROXAR.

In an exemplary embodiment, the modified ER probe can use the electrical resistance technique as an "on-line" method for monitoring the rate of corrosion and metal loss for equipment including one or more metallic structures or components of the ER probe, where the ER probe includes an appropriate measurement system to measure the electrical resistance of the element. Reduction (metal loss) in the cross section of the element of the ER probe due to corrosion increases the elements electrical resistance. Measurements showing an increase in the electrical resistance indicates that the element is corroding, which can be due to the oxidizing biocide interaction with the element. Monitoring the electrical resistance over a time period correlates to the rate of corrosion. Once the rate of corrosion is known, the amount of biocide being used can be adjusted.

FIG. 1 illustrates a cross-sectional view of an exemplary embodiment of the present disclosure. In an exemplary embodiment, the modified ER probe includes a ER probe and a cooling unit that includes a structure, preferably a mantel with an annular cavity disposed or arranged around the ER probe, so that the temperature of the surface can be controlled and, optionally, a temperature sensor (not shown) to monitor the temperature. As mentioned above, the ER probe includes one or more elements, where the resistance across the electrode can be determined and/or measured by the modified ER probe or computer system interfaced with the modified ER probe.

In an embodiment, there is a cavity between a portion of or all of the structure and the ER probe. In an embodiment, the distance between the structure and the ER probe can be about 1 mm to 100 cm. In an embodiment, the structure can be contoured to flow the cooling medium. In an embodiment, the structure can have a cross section that is similar to the ER probe cross section. In an embodiment, the structure can have a circular cross section, polygonal cross section or the like. In an embodiment, the structure can include one or more openings so that a cooling medium, e.g., a gas or a fluid, can flow in and out of the cavity of the structure. In addition, the cooling unit includes an opening for the ER probe so that the sensor (e.g., element) of the probe (See the rectangular shaped structure in FIG. 2) is exposed to the environment around the ER probe. In an embodiment, the openings can be the same or a different size (e.g., circular, polygonal, and the like) and on the order of millimeters to centimeters. In an embodiment, the structure can have 1 to 100 openings. In an embodiment, a flow system can be used to flow the cooling medium and can include flow regulators, piezoelectric systems, and the like.

In an embodiment a surface of the cooling unit, which has been cooled down to a specified temperature, is arranged to be in connection, preferably directly attached (touch), with a surface of the probe thereby cooling the probe head and the sensing element. In an alternative embodiment, the cooling unit is not in direct contact with the ER probe, so a cool gas, preferably air, can be circulated in the area around the ER probe to control the temperature of the ER probe. The modified ER probe can also include a temperature sensor so that the temperature can be monitored as a function of the results produced by the ER probe.

In an embodiment, the temperature sensor can include one or more temperature detection sensors disposed on or outside of the modified ER probe. In an embodiment, the temperature measurement sensor(s) can be disposed adjacent the ER probe to measure the temperature of one or more of the following: the ER probe, the air around the ER probe, or the air outside of the ER probe.

Figures 2A, 2B:
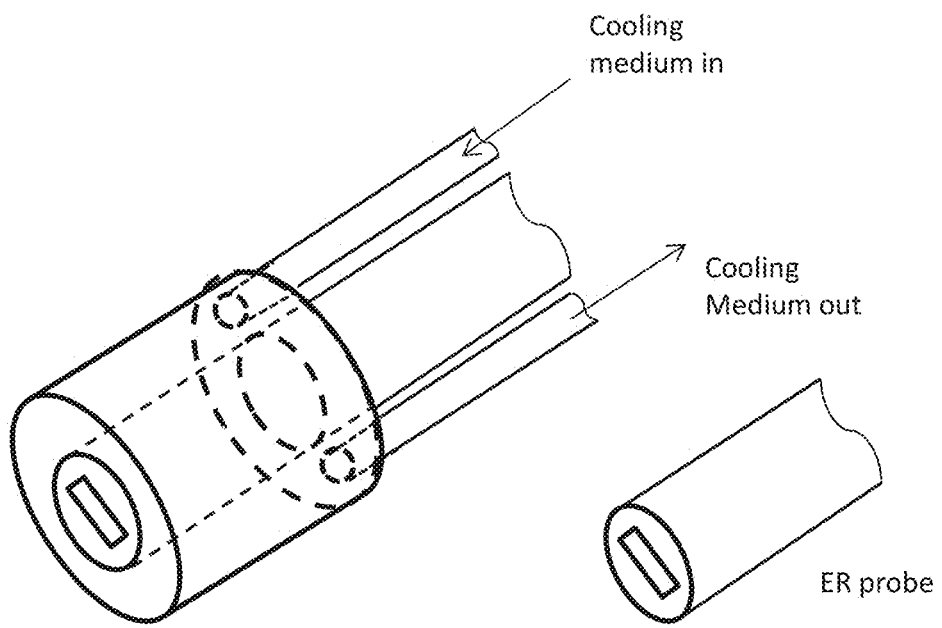
FIG. 2A illustrates a perspective view of the modified ER probe (i.e., an embodiment of a cooling unit is disposed around the ER probe).
FIG. 2B illustrates a schematic perspective view of an ER probe.

FIG. 2A illustrates a perspective view of an embodiment of the modified ER probe (i.e., an embodiment of a cooling unit is disposed around the ER probe). FIG. 2A illustrates an embodiment of a configuration to change the temperature (e.g., reduce the temperature) using the cooling unit by flowing a cooling medium through the structure. FIG. 2B illustrates a schematic perspective view of an ER probe.

It has been found that an ER probe simply installed in the hottest parts of a paper or board machine may not reliably show corrosion rate and quantity as the sensor surface will be too hot and dry. It has been found that the most severe corrosion damages caused by oxidizing biocides show up on those surfaces where condensate water is formed due to the slightly lower surface temperature than in the surrounding very hot air in the beginning of a dryer section, for example.

Embodiments of the present disclosure may overcome these problems by cooling the measurement head of the ER probe. Although not intending to be bound by theory, cooling the ER probe can create conditions where a sensing element in the ER probe is sensitive to reacting to changes in the amount of corrosive chemicals in the air and thus gives information on the rate of vapor phase corrosion in the paper machine. In an embodiment, the temperature difference between the air outside of the modified ER probe and the surface of the ER probe can be controlled to be about 3 to 30° C.

It was also learned that a small temperature change in the measurement surface of the ER probe can impact the measurement results. For example a malfunctioning of the cooling system or unintentional change in the cooling adjustment could change the temperature of the ER probe surface to an extent that it impacts formation of condensate water and thus impacts measurement. In an embodiment, an automatic valve assembly for a cooling water flow can be controlled and maintain the probe surface temperature as constant. In an embodiment, the variation of probe surface temperature can be controlled to be about 10° C. or less.

In an exemplary embodiment, this aspect can be solved by installing an on-line temperature measurement sensor in the modified ER probe. In an embodiment, a change in the rate of vapor phase corrosion can be considered as valid data when the temperature of the sensor head was unchanged (e.g., a temperature change of about 10° C. or less or about 3° C. or less) from adjacent temperature readings. This provides reliable information on changes in the rate of vapor phase corrosion and this data can be used for adjusting dosages of oxidizing biocides. For example, if vapor phase corrosion shows an increased rate for about 12 hours compared to the preceding 12 hours (and the temperature change of the is less than 5 or 3° C.), this may indicate that the dosing of oxidizing biocides can be reduced (e.g., nearest to the headbox of the paper machine). This is just an example of the possible time ranges set for data comparison, depending on the paper machine conditions the time range in comparison can be shorter (e.g., 1 to 12 hours) or longer (e.g., 12 hours to day increments or 2 or 3 day increments, or a week increment).

In an embodiment, the signals from the modified ER probe and the signals from the temperature sensor are stored in a computer device (e.g., software, hardware, or a combination thereof). The computer device can collect, store, and analyze the signals, e.g., rate of vapor phase corrosion and/or change in corrosion quantity is calculated using signals from modified ER probe. In addition, the computer device can also be used for signals from the temperature sensor, to check validity of the detected rate of vapor phase corrosion. In an embodiment, adjustment of the biocide dosing amounts can be determined from the corrosion data (e.g., calculated data or untreated data from the modified ER probe). The adjustment can happen automatically, such as initiated by the computer device, or manually, such as initiated by a person. In an embodiment where manual dosing is used, the computer device is programmed to send an alarm message for a service person, which after receiving a message of, e.g., increased corrosion rate, can then go and manually adjust biocide dosing quantities to a lower level. In an embodiment for the automatic dosing control, a computer device monitoring the signals from the modified ER probe and temperature sensor can be used to convert the information on changes in corrosion data (i.e., corrosion quantity or corrosion rate) into relative changes in biocide dosing quantities to the paper making process. In this regard, the system is completely automated.

Figure 5:
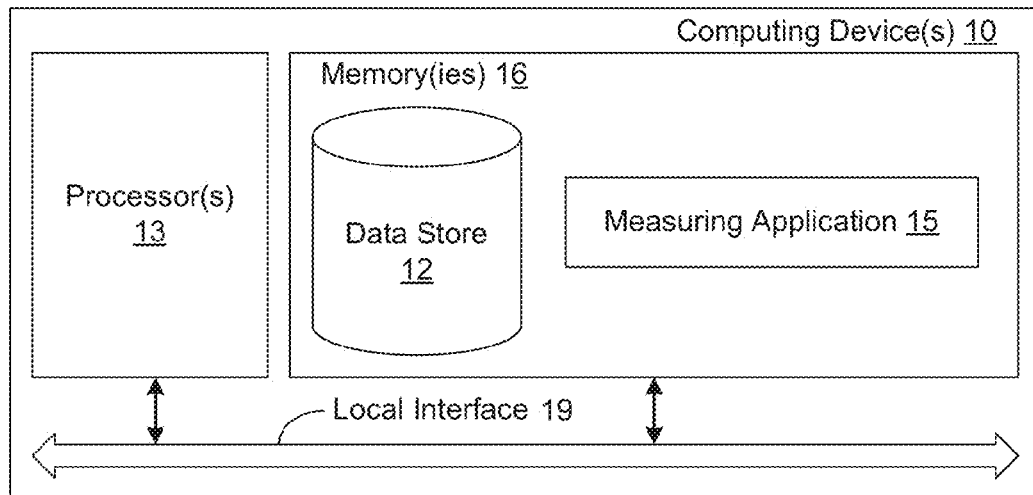
FIG. 5 is a schematic of a measurement system including a computer device.

Referring to FIG. 5, in an embodiment, the modified ER probe system 200 may be in communication with the computer device 10. In particular, the temperature sensor 210 and the cooling unit 220, and the modified ER probe 230, may be communication with the computer device 10.

In an exemplary embodiment, one or more aspects of the measuring method (e.g., measuring application 15) can be implemented using software and/or hardware as described herein.

With reference to FIG. 5, shown is a schematic block diagram of a computing device 10 according to various embodiments of the present disclosure. The computing device 10 includes at least one processor circuit, for example, having a processor 13 and a memory 16, both of which are coupled to a local interface 19. To this end, the computing device 10 may comprise, for example, at least one server computer or like device. The local interface 19 may comprise, for example, a data bus with an accompanying address/control bus or other bus structure as can be appreciated.

Stored in the memory 16 are both data and several components that are executable by the processor 13. In particular, stored in the memory 16 and executable by the processor 13 are a measuring application 15 and/or other applications. Also stored in the memory 16 may be a data store 12 and other data. In addition, an operating system may be stored in the memory 16 and executable by the processor 13.

It is understood that there may be other applications that are stored in the memory 16 and are executable by the processor 13 as can be appreciated. Where any component discussed herein is implemented in the form of software, any one of a number of programming languages may be employed such as, for example, C, C++, C#, Objective C, Java®, JavaS-cript®, Perl, PHP, Visual Basic®, Python®, Ruby, Delphi®, Flash®, MATLAB, or other programming languages.

A number of software components can be stored in the memory 16 and are executable by the processor 13. In this respect, the term "executable" means a program file that is in a form that can ultimately be run by the processor 13. Examples of executable programs may be, for example, a compiled program that can be translated into machine code in a format that can be loaded into a random access portion of the memory 16 and run by the processor 13, source code that may be expressed in proper format such as object code that is capable of being loaded into a random access portion of the memory 16 and executed by the processor 13, or source code that may be interpreted by another executable program to generate instructions in a random access portion of the memory 16 to be executed by the processor 13, etc. An executable program may be stored in any portion or component of the memory 16 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 16 is defined herein as including both volatile and nonvolatile memory and data storage components. Volatile components are those that do not retain data values upon loss of power. Nonvolatile components are those that retain data upon a loss of power. Thus, the memory 16 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 13 may represent multiple processors 13 and the memory 16 may represent multiple memories 16 that operate in parallel processing circuits, respectively. In such a case, the local interface 19 may be an appropriate network that facilitates communication between any two of the multiple processors 13, between any processor 13 and any of the memories 16, or between any two of the memories 16, etc. The local interface 19 may comprise additional systems designed to coordinate this communication, including, for example, performing load balancing. The processor 13 may be of electrical or of some other available construction.

Although the measuring application 15 and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Figure 6:
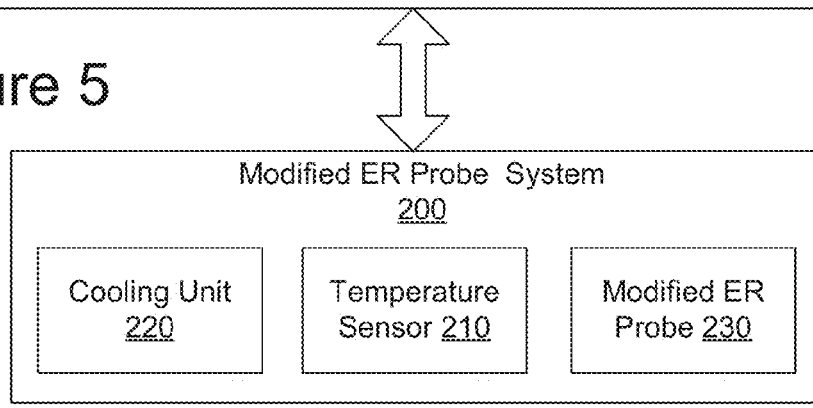
FIG. 6 is a flow chart of an example of monitoring the vapor phase corrosion.
Figure 6:
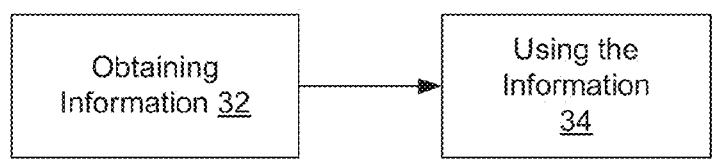

Referring to FIG. 6, in an exemplary embodiment, a measuring application 15 can be used for monitoring and/or measuring the vapor phase corrosion in a paper or board machine. In an exemplary embodiment, a step 32 includes obtaining information regarding the rate of vapor phase corrosion over a time period. In a step 34, the information can be used to determine how to adjust the dosing of an oxidizing biocide in a paper or board making process. Each of these features and others as they relate to the monitoring the vapor phase corrosion is described herein in more detail, specifically, in regard to the discussion regarding obtaining information.

Although the flowchart of FIG. 6 shows a specific order of execution, it is understood that any number of counters, state variables, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the measuring application 15 and/or application(s), that comprises software or code can be embodied in any non-transitory computer-readable medium for use by or in connection with an instruction execution system such as, for example, a processor 13 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

The present invention is further described in more detail by the following examples which are not intended to limit the present invention.

Example 1

Figure 3:
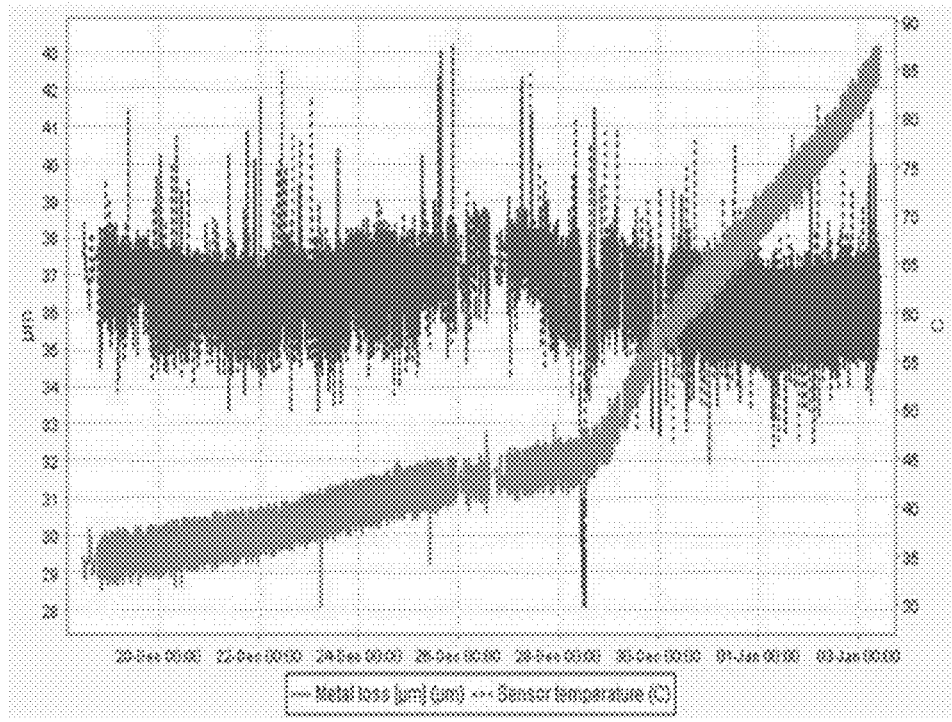
FIG. 3 illustrate a graph showing example data about measured rate of corrosion (metal loss of the sensing element, μm) during a period from $18^{th}$ of December to $3^{rd}$ of January.

An Electrical Resistance (ER) probe (Roxar Flow Measurements AS, Norway) modified with a cooling unit, with a pt-temperature probe and with a datalogger, was installed in a paper machine making almost 150 000 tons of paper annually. Exact point of installation was in the beginning of the drier section, inside the protective doors of the drier section, in vapor phase, less than one meter away from the paper web. The sensing element of the ER probe was of carbon steel. Surface temperature of the sensing element was lowered and kept constant, around 60° C., by cooling water flow. Datalogger was recording temperature and rate of corrosion (metal loss) every minute. Datalogger was connected to internet and enabled remote on-line monitoring of the vapor phase corrosion. The graph shown in FIG. 3 illustrates example data about measured rate of corrosion (metal loss of the sensing element, μm) during a period from $18^{th}$ of December to $3^{rd}$ of January. It can be seen from the FIG. 3 that until $29^{th}$ of December the rate of vapor phase corrosion was quite stable, cumulative metal loss increased linearly and daily average metal loss was ca. 0.3 μm/d. When biocide dosages in the machine were changed after a shut-down of the machine late of December $29^{th}$, the on-line probe for vapor phase corrosion responded quickly and showed an increased rate of vapor phase corrosion. Temperature measurements are used for validating the data and they did not show any significant changes in the probe temperature (except the temporary cooling during machine shutdown), thus indicating that rate of corrosion was changed due changes in chemistry of the vapor phase. Situation was followed on-line and measurements of the next few days confirmed that corrosion rate truly increased from ca. 0.3 μm/d to a level of ca. 2.0 μm/d, encouraging to quickly adjust biocides feed. These measurements demonstrate that with this innovative equipment the rate of vapor phase corrosion of a paper machine can be monitored on-line, and thanks to its sensitivity the impact of changes such as adjustment of biocide feed can be quickly measured. This information can be used for adjusting biocide dosing to the paper machine, enabling to minimize rate of vapor phase corrosion, proactively before the whole machine shows signs of corrosion.

Example 2

Figure 4:
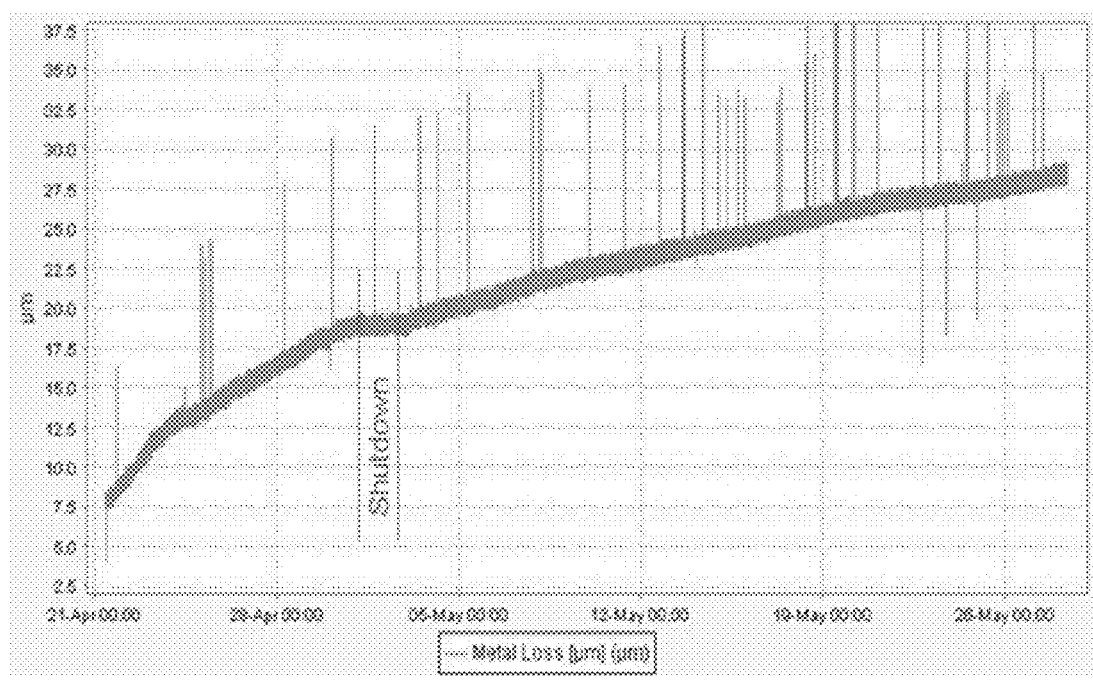
FIG. 4 illustrates a graph that shows example data about measured rate of corrosion (metal loss of the sensing element, μm) during a five-week period.

A modified ER probe (similar setup like in example 1) was installed in vapor phase in beginning of the drier section, near the $6^{th}$ cylinder, of a board machine making almost 160 000 tons of packaging board annually. Datalogger was recording rate of corrosion (metal loss) every minute. Datalogger was connected to internet and enabled remote on-line monitoring of the vapor phase corrosion. FIG. 4 illustrates a graph that shows example data about measured rate of corrosion (metal loss of the sensing element, μm) during a five-week period. It can be seen from FIG. 4 that during the first ten days the rate of vapor phase corrosion was quite high, with a daily average metal loss of 1.17 μm/d. The biocide program was altered during shut-down of the machine and starting from re-start of the machine ($3^{rd}$ of May) the rate of vapor phase corrosion was clearly lower, with a daily average metal loss of 0.25 μm/d. These measurements demonstrate that with this innovative equipment the rate of vapor phase corrosion of a board machine can be monitored on-line, and thanks to its sensitivity the impact of changes such as adjustment of biocide feed can be quickly measured. In this case it was possible to demonstrate within one day only that the change in the biocide program resulted in increased corrosion safety of the actual paper machinery.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'". When a range includes "zero" and is modified by "about" (e.g., about one to zero or about zero to one), about zero can include, 0, 0.1, 0.01, or 0.001.

While only a few embodiments of the present disclosure have been shown and described herein, it will become apparent to those skilled in the art that various modifications and changes can be made in the present disclosure without departing from the spirit and scope of the present disclosure. All such modification and changes coming within the scope of the appended claims are intended to be carried out thereby.

The invention claimed is:

1. A method for monitoring the vapor phase corrosion in a paper or board machine, comprising:
obtaining, using a modified electrical resistance (ER) probe equipped with an ER probe and a cooling unit disposed around the ER probe, information regarding the rate of vapor phase corrosion over a time period; and
using the information to determine how to adjust the dosing of an oxidizing biocide in a paper or board making process
and
adjusting the amount of the oxidizing biocide based on the information obtained regarding vapor phase corrosion.

2. The method of claim 1, wherein the information is obtained using a temperature measurement sensor to measure the temperature of one or more of the following: the ER probe, the air around the ER probe, or the air outside of the ER probe.

3. The method of claim 2, further comprising: controlling the temperature difference between the air outside of the modified ER probe and the surface of the ER probe.

4. The method of claim 1, further comprising:
adjusting the amount of the oxidizing biocide based on the information obtained regarding vapor phase corrosion.

5. The method of claim 1, wherein obtaining includes measuring an electrical resistance of an element in the modified ER probe.

6. The method of claim 5, wherein an increase in the electrical resistance of the element over a time period indicates that the element was undergone reduction, and wherein a rate of corrosion is determined from the reduction of the element over the time period.

7. A method of claim 1, wherein
obtaining information regarding the rate of vapor phase corrosion over a time period is by a computing device; and
using the information to determine how to adjust the dosing of an oxidizing biocide in a paper or board making process is by a computing device.

8. The method of claim 7, further comprising:
adjusting, by the computing device, the amount of the oxidizing biocide based on the information obtained regarding vapor phase corrosion.

9. The method of claim 8, wherein obtaining includes measuring, by the computing device, an electrical resistance of an element in a modified ER probe.

10. The method of claim 8, further comprising: controlling, by a computing device, the temperature difference between the air outside of a modified ER probe and a surface of an ER probe.

* * * * *